(12) United States Patent
Clark

(10) Patent No.: US 8,409,529 B2
(45) Date of Patent: Apr. 2, 2013

(54) HISTOLOGY SLIDE AND PARAFFIN BLOCK PROTECTOR AND TRANSPORT SLEEVE

(75) Inventor: Noel D. Clark, Riverview, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 0 days.

(21) Appl. No.: 13/525,925

(22) Filed: Jun. 18, 2012

(65) Prior Publication Data
US 2012/0258027 A1 Oct. 11, 2012

Related U.S. Application Data

(63) Continuation of application No. PCT/US2010/061200, filed on Dec. 20, 2010.

(60) Provisional application No. 61/287,970, filed on Dec. 18, 2009.

(51) Int. Cl.
*B01L 3/00* (2006.01)
(52) U.S. Cl. ........... 422/560; 422/547; 422/500; 422/50
(58) Field of Classification Search .................. 422/560, 422/547, 500, 50
See application file for complete search history.

(56) References Cited

U.S. PATENT DOCUMENTS

| 2,996,762 A | 8/1961 | McCormick |
| 5,192,503 A | 3/1993 | McGrath et al. |
| 5,626,630 A | 5/1997 | Markowitz et al. |
| 5,855,609 A | 1/1999 | Knapp |
| 2009/0246825 A1 | 10/2009 | McCormick |

FOREIGN PATENT DOCUMENTS

| JP | 09145571 A | 6/1997 |
| JP | 2007147399 A | 6/2007 |
| JP | 2007255896 A | 10/2007 |

OTHER PUBLICATIONS

International Search Report with a mailing date of Sep. 29, 2011 for International Application PCT/US2010/061200 with a filing date of Dec. 20, 2010.

*Primary Examiner* — Christine T Mui
(74) *Attorney, Agent, or Firm* — Robert J. Varkonyi; Smith & Hopen, P.A.

(57) ABSTRACT

A protective sheath for prolonged storage of pathology paraffin blocks. The sheath protects the paraffin block against gouging, scratching, denting, rodents, and insects. A pathology slide slides into slots in the protective sheath fixing the slide into position in protective sheath. Fixation points are built on the side of the slide to allow a user or automated system to place and retrieve protective sheath.

28 Claims, 17 Drawing Sheets

HISTOLOGY SLIDE AND PARAFFIN BLOCK PROTECTOR AND TRANSPORT SLEEVE

CROSS REFERENCE TO RELATED APPLICATIONS

This application is a continuation of prior filed International Application, Serial Number PCT/US2010/061,200 filed Dec. 20, 2010, which claims priority to U.S. provisional patent application 61/287,970 filed Dec. 18, 2009, which are herein incorporated by reference.

FIELD OF INVENTION

The invention related to histology sample storage. Specifically, the invention is a protective sleeve for stored paraffin blocks and histology slides.

BACKGROUND OF THE INVENTION

Each day, tens of thousands of patients go through inpatient and outpatient procedures resulting in either biopsies or excised tissues. These tissues are subsequently processed and embedded in paraffin blocks to facilitate cutting of pathological slides used in diagnostic and research applications. The samples may be fresh or fixed. In order to facilitate visualizing these cells by microscopic examination, the cells/tissue must first be processed and embedded in a carrier medium to allow cutting after paraffin embedding. After the specimen has been collected, the tissue sample is fixed and dehydrated to preserve tissue components. The tissue sample is then passed through fixatives to remove water from the sample, and then processed with a solvent to dissolve fatty materials and "clear" the tissue sample. After being "cleared", the tissue sample is placed in molten paraffin and it is infiltrated with the wax, which replaces the solvent which will evaporate or be diluted to trace levels, causing all the tissue to be infiltrated with a common wax binder. The sample may then be cut in a section plane to be presented to the microtome blade for creation of a microscope slide, which may be examined microscopically for information collection.

The preparation of a histology specimen includes treating the tissue with a variety of chemicals, followed by embedding the tissue into a capsule of low-melting-point paraffin wax. The wax capsules which form the specimen samples are cast is small containers called "boats", or in two-piece containers such as those described in McCormick (U.S. Pat. No. 2,996, 762). A microtome is used to cut thin slides of the embedded tissue, which are then mounted onto slides for microscopic study. The remainder of the embedded tissue specimen is stored for future use and reference.

A variety of automated systems have been developed for use in histology laboratories for labeling slides prior to mounting specimens to the slides. Many of the systems focus on labeling the slide with specific information, such as patient information and tissue type or a printed bar code which may be scanned to obtain the patient database records.

These blocks and slides are soon thereafter manually filed and archived into one of several plastic, metal, or cardboard filing/storage systems. As a general rule of policy and law, the blocks and slides are retained for as many as 10 years or longer. Systems are known that permit processing of tissue samples, such as those described in McCormick (U.S. application Ser. No. 12/425,583). During this filing process the blocks, which have a wax/paraffin media can be damaged. The blocks can be scratched, gouged, dislodged from the parent cassette, or even melted, if the temperature of the storage location is too hot. In addition, other hazards of storage may arise with long-term conditions. These may include, but are not limited to, insect damage, rodent threat and damage, and dirt and debris in the storage location.

Later, when the block is needed for additional staining or review purposes, the block will be handled again and subjected to the same handling/storage conditions. Normally, the administrative person pulling the block will leave a tag indicating that the block has been removed and for whom the block was pulled (the requesting pathologist's name). This is supposed to give a tracking aspect to the storage system. However, as human nature would allow, this seldom is achieved and blocks go unaccounted for and then time is wasted tracking down the person or office which now possesses the block. In addition, current storage systems tightly store the histology sample paraffin blocks, to save on storage space. As a consequence of this tight fit, if the person does place a "pulled" tag in the area, most of the time the tag gets pulled away by constant opening and closing of the tray/drawer. The same holds true for the pathology slides which were created from the parent block.

Therefore, the art is underdeveloped for long-term paraffin block storage which allows easy identification of the sample, sample location, and safe storage conditions.

SUMMARY OF INVENTION

The present invention provides a protective sheath for prolonged storage of pathology paraffin blocks. This device will remedy the situation by having a protective sleeve which, not only holds the parent block, but also holds the original H&E slide created from it. If the H&E slide is pulled for a pathologist, the person now has a slot to place the tag and it stays with the parent block. If the block and slide are pulled simultaneously, an empty protective sleeve can be placed in the drawer with a pull tag placed in it.

The protective sheath is constructed with a first protective member and connected second protective member. The first protective member is shaped like an open box, having a first vertical wall and second vertical wall, each with an upper edge, a lower edge, a transverse edge and an opening edge. A first upper horizontal wall is connected to the upper edge of the first and the second vertical walls, with a first lower horizontal wall connected to the lower edge of the first and the second vertical walls. A transverse wall is connected to the transverse edge of the first and the second vertical walls, such that the walls form a box. At least one opening is disposed in the upper horizontal wall and adapted to accept a tissue slide. In some embodiments, the edges of the at least one tissue slide opening are coated with a compound, such as Teflon, polyester, para-phenylenediamine, terephthaloyl chloride polymer, carbon fiber, expanded PTFE, meta-phenylenediamine, nylon, polypropylene, latex, silicone, polyurethane, polyisoprorene polyvinylchloride, ethylene propylene diene monomer, styrene, cornstarch powder, graphite, meta-aramid compounds, or para-aramid compounds. The first protective member may also include at least one slot disposed on the lower horizontal wall adapted to accept a tissue slide. The at least one slot may correlate to the at least one tissue slide opening, and may also include a similar coating to the tissue slide opening.

The second protective member is also shaped like a box adapted to accept a paraffin block, and attached to the transverse wall of the first protective member. The second protective member has a third vertical wall and fourth vertical wall having an upper edge, a lower edge, and a transverse edge. A second upper horizontal wall connected to the upper edge of the third vertical wall and fourth vertical wall, with a second lower horizontal wall connected to the lower edge of the third vertical wall and fourth vertical wall. A transverse wall is connected to the transverse edge of the third and the fourth vertical walls to form the box. The second protective member may be dimensioned to accept a paraffin block, or alternatively has a support structure disposed in the interior of the second protective member. Where a support structure is disposed in the interior of the second protective member the paraffin support structure comprises an integrated support having a support wall disposed on the interior face of the third and fourth vertical walls, such that the space defined between the third and fourth vertical walls and the second lower horizontal wall and the support wall are dimensioned to accept a paraffin block. The support may instead be partially integrated into the second protective member and comprises a fifth and sixth vertical walls disposed in the interior space of the second protective member, having an upper edge and a lower edge. A first support wall disposed on the upper edge of the fifth vertical wall and sixth vertical wall, with a second support wall disposed on the lower edge of the fifth vertical wall and sixth vertical wall. In this embodiment the support walls and fifth and sixth vertical walls are disposed on the second transverse wall of the second protective member and the walls dimensioned to accept a paraffin block. Alternatively, the support is a distinct support attached to the second support. In this embodiment, a fifth and sixth vertical walls are disposed in the interior space of the second protective member, having an upper edge, a lower edge, and a transverse edge. A first support wall is connected to the upper edge of the fifth vertical wall and sixth vertical wall; with a second support wall connected to the lower edge of the fifth vertical wall and sixth vertical wall. A third transverse wall is connected to the transverse edge of the fifth and sixth vertical walls, and also connected to the second transverse wall of the second protective member. The support is dimensioned to accept a paraffin block.

The protective sheath may also include at least one handling point disposed on the first and the second vertical walls of the first protective member, or alternatively disposed on the third and the fourth vertical walls of the second protective member. The handling points may be any handling system known to one in the art, such as a plurality of holes, handles, at least one hook, at least one bracket, or a plurality of tubes extending from the first vertical wall to the second vertical wall. In some embodiments, the sheath possesses a series of fixation points that permit a user or robotic arm to retrieve and place the sheaths. Currently, steps are underway nationally and internationally, to create biobanking warehouses. The sheath design facilitates and accommodates use of an automated paraffin block storage system. Some of these warehouses will hold, literally, hundreds of thousands of specimens, either in a frozen storage condition or as a paraffin block and its resultant slides. With this massive volume of tissues to be considered, the inevitable creation of automated storage systems for paraffin blocks will arise. Currently there are robotic freezers with mechanisms which allow a person to place and retrieve specimens without contact (remotely, though within several feet of the storage medium). A robotic arm grasps the storage rack filled with vials of frozen tissue or liquids and either places it in the freezer or returned it to the requestor. The same robotic arm could also do this feature for paraffin block storage. As a final feature, the device includes a design aspect which will allow the sleeve to be used in such an automated storage capacity.

The protective sheath may also include a protective shield. The protective shield is either a hingedly connected or slidingly connected to the protective sheath. Where the protective shield hingedly connects, the protective shield has a first face adapted to hingedly engage the first upper horizontal wall and a second face disposed perpendicular to the first face and adapted to cover the open face of the first protective member. The protective shield may connect to the protective sheath using pins, screws, or hinges. Where the protective shield slidingly connects, the protective shield has a pair of rails disposed on the first and second vertical walls along the open face of the first and second vertical walls and a protective face adapted to engage the pair of rails.

In another embodiment of the invention, the protective sheath includes a first protective member, a sheath body, and a second protective member. The first protective member has a first vertical wall and second vertical wall, each having an upper edge, a lower edge, a transverse edge and an opening edge. A first upper horizontal wall is connected to the upper edge of the first and the second vertical walls, with a first lower horizontal wall connected to the lower edge of the first and the second vertical walls. A first transverse wall is connected to the transverse edge of the first and the second vertical walls, such that the walls define a box. The first protective member has at least one opening disposed in the upper horizontal wall and adapted to accept a tissue slide. In some embodiments, the edges of the at least one tissue slide opening are coated with a compound, such as Teflon, polyester, para-phenylenediamine, terephthaloyl chloride polymer, carbon fiber, expanded PTFE, meta-phenylenediamine, nylon, polypropylene, latex, silicone, polyurethane, polyisoproprene polyvinylchloride, ethylene propylene diene monomer, styrene, cornstarch powder, graphite, meta-aramid compounds, or para-aramid compounds. The first protective member may also include at least one slot disposed on the lower horizontal wall adapted to accept a tissue slide. The at least one slot may correlate to the at least one tissue slide opening, and may also include a similar coating to the tissue slide opening.

The sheath body has a third vertical wall and fourth vertical wall, each having an upper edge, a lower edge, a transverse edge and an opening edge. A second upper horizontal wall connected to the upper edge of the third and the fourth vertical walls, and a second lower horizontal wall connected to the lower edge of the third and the fourth vertical walls. A second transverse wall is connected to the transverse edge of the third and the fourth vertical walls, such that the walls define a box. At least one handling point disposed on the third and the fourth vertical walls. Some exemplary handling points include a plurality of holes, at least one hook, at least one bracket, at least one handle, or a plurality of tubes extending from the first vertical wall to the second vertical wall. The sheath body attaches to the first protective member's first transverse wall via the opening edge of the third vertical wall and fourth vertical wall.

The second protective member disposed on the second transverse wall of the sheath body, and is comprised of a fifth vertical wall and sixth vertical wall having an upper edge, a lower edge, and a transverse edge. A third upper horizontal wall is connected to the upper edge of the fifth vertical wall and sixth vertical wall, with a third horizontal wall connected to the lower edge of the fifth vertical wall and sixth vertical wall. A third transverse wall is connected to the transverse edge of the fifth vertical wall and sixth vertical walls, such that the walls define a box and where the second protective member is dimensioned and adapted to accept a paraffin block.

The protective sheath may also include a protective shield. The protective shield is either a hingedly connected or slidingly connected to the protective sheath. Where the protective shield hingedly connects, the protective shield has a first face adapted to hingedly engage the first upper horizontal wall and a second face disposed perpendicular to the first face and adapted to cover the open face of the first protective member. The protective shield may connect to the protective sheath using pins, screws, or hinges. Where the protective shield slidingly connects, the protective shield has a pair of rails disposed on the first and second vertical walls along the open face of the first and second vertical walls and a protective face adapted to engage the pair of rails.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
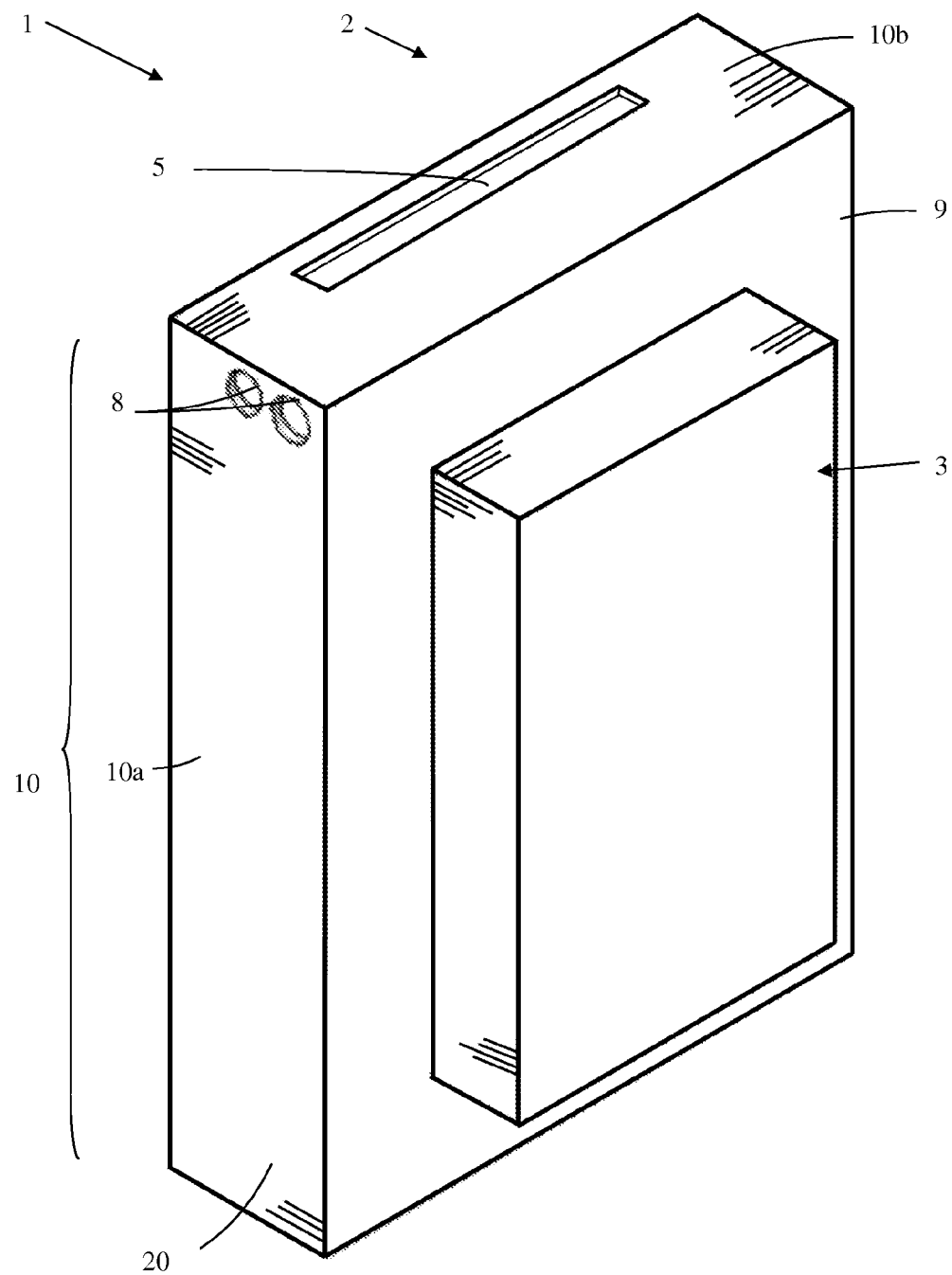
FIG. 1 shows an isometric wireframe view of the protective sheath looking across the back side of the present invention from above. The pathology slide is depicted partially inserted into the sheath.

A device, or sheath, is designed to store and protect histology slides and histology samples from gouging, scratching, denting, rodents, insects, and other damage. The sheath is comprised of two sections, one of which is designed and adapted to accept the histology slides. A second section of the sheath has storage for a histology sample. It is noted that this second section may extend out from the remainder of the sheath, or it may be integrated into another section of the sheath. A tube may optionally be included on one edge of the histology sample storage section, thereby reducing or eliminating possible vacuum build-up when removing the paraffin histology sample. The sheath protects the paraffin block and histology slide from abuse and will not require measures to compensate for that abuse. Also, this will improve the efficiency of the office environment and greatly accommodate a more adaptive tracking system for monitoring block's storage and usage, while also creating a path to future automation. The sheath also protects the paraffin block against gouging, scratching, denting, rodents, and insects.

The sheath may be made of any material known in the art. Some examples include plastics such as polyethylene, polypropylene, polyethylene terephthalate, polyvinylchloride, polyvinylidenechloride, polycarbonate, polyurethane, polyamide, polytetrafluoroethylene, polyvinylacetate, wood, ceramic, cellulose materials such as cardboard, fiberboard, metal such as titanium, stainless steel, and surgical steel. Specific embodiments are envisioned constructed of plastic.

The first section of the sheath, comprising the histology slide storage contains at least one opening provided in the upper wall of this section for storing a slide. However, multiple openings may be provided, allowing for multiple histology slides to be stored. In some embodiments of the sheath, the upper slot may include a coating on the edges of the slot to allow easy removal and insertion of a histology slide. Examples of coatings include, but are not limited to, Teflon, polyester, para-phenylenediamine, terephthaloyl chloride polymer, carbon fiber, expanded PTFE, meta-phenylenediamine, nylon, polypropylene, latex, silicone, polyurethane, polyisoproprene polyvinylchloride, ethylene propylene diene monomer, styrene, cornstarch powder, graphite, meta-aramid compounds like Nomex™, and para-aramid compounds like Kevlar™. The histology slide storage also may include a lower slot, formed as a depression in the lower wall such that a histology slide is fixed into position by the upper slot and lower slot. Where multiple upper slots are provided, an equal number of corresponding lower slots may also be included. In embodiments possessing at least one lower slot, the lower slot may also include the aforementioned coating in addition to, or instead of, the upper slot The protective sheath may be formed by any suitable means known in the art, taking into account the material the sheath is manufactured from. For example, where the sheath is made from a polymer material, the sheath may be formed using a mold with the polymer applied to the mold under appropriate heat and pressure to allow curing of the polymer. Other means of forming the sheath using polymers and resins includes extrusion molding, vacuum forming, thermoforming, and injection molding. Metals and cellulose materials may be formed using a die or compression molded.

A protective face may also be used with the sheath. The protective face may slide into place, using for example rails disposed on the open face of the sheath, or the protective face may hinge into place. In the latter example, the protective face may be attached as known in the art to allow the face to swing. Non-limiting examples include pins, screws, or hinges integrated into the protective face. The hinges may be placed on the sides of the sheath, or on the upper wall. In specific embodiments, the protective face may cover the slide openings in the upper wall, thereby locking the slides into place when the protective face is in a lowered position.

The protective face may be made of any suitable material. Examples include polyethylene, polypropylene, polyethylene terephthalate, polyvinylchloride, polyvinylidenechloride, polycarbonate, polyurethane, polyimide, polytetrafluoroethylene, polyvinylacetate, wood, ceramic, cellulose materials such as cardboard, fiberboard, metal such as titanium, stainless steel, surgical steel, however transparent materials are preferred so as to allow a user to visualize the contents of the sheath with the face in a lowered position. Moreover, where a transparent material is used, when the slide and/or paraffin sample are removed, a tag or other information relating to the location of the missing slide may be easily visualized without opening the protective face.

The sheath may incorporate a slide retention system to lock the slides into the first protective member. The retention system may be a clip, such as those shown in FIGS. 10-18. The retention system may be disposed on the transverse wall where the upper slide opening is adjacent to the transverse wall. In such embodiments, the retention system is generally mounted vertically, such that the top of a slide interacts with the retention system to prevent the slide from moving. The retention system may also be mounted onto the upper wall of the first protective member, adjacent to each upper slide opening. In this configuration, the retention system is generally mounted horizontally, and interacts with the top of the slide to prevent movement of the slide. The retention system may be a clip or other system known in the art. The clip or other retention system may have an angled face, allowing the slide to push the retention system away from the upper slide opening when being inserted. The adjacent face is flat, to interact with the top of the slide.

Identification means may be included on the sheath, such as bar code, medical information transponder, such as those described by Knapp (U.S. Pat. No. 5,855,609) and Markowitz, et al. (U.S. Pat. No. 5,626,630), or patient code or information. The identification is optionally included on the side of the sheath, allowing a plurality of sheaths to be stored side-by-side, while concurrently providing easy identification of the patient or histology information of the sample contained in the sheath.

In some embodiments of the invention, fixation points are provided to allow a user or automated system to place and retrieve the sheath. Exemplary fixation points include dual holes for a robotic arm, hooks, and brackets. However, any system known in the art that allows the block to be positioned without concern for the center of gravity is envisioned.

As used herein, "about" means approximately or nearly and in the context of a numerical value or range set forth means±15% of the numerical.

As used herein, "substantially" means largely if not wholly that which is specified but so close that the difference is insignificant, and such differences do not influence the functional properties of the term beyond the normal tolerances permitted by one of skill in the art. In some embodiments, "substantially" means that the differences do not vary by more than 10% or less.

Example 1

Sheath 1 comprises body 2 and paraffin block sleeve 3, as seen in FIG. 1. Body 2 includes a transverse wall 9 and circumscribing wall 10 of a first horizontal wall 10*a*, an upper wall 10*b*, a second horizontal wall 10*c*, and a lower wall 10*d*, thereby forming an "open box" and defining an inner space in body 2. Optional identifier 20 is disposed on first horizontal wall 10*a*. Body 2 integrates slide storage system 4. Upper slide opening 5 is disposed on upper wall 10*b* and dimensioned to accept a pathology slide. Lower slide receiving face 6 is disposed on the inner face of lower wall 10*d*, providing a surface elevated from lower wall 10*d*. Lower slide opening 7 is provided in lower slide receiving face 6 and consists of a detent dimensioned to accept a pathology slide.

Figure 2:
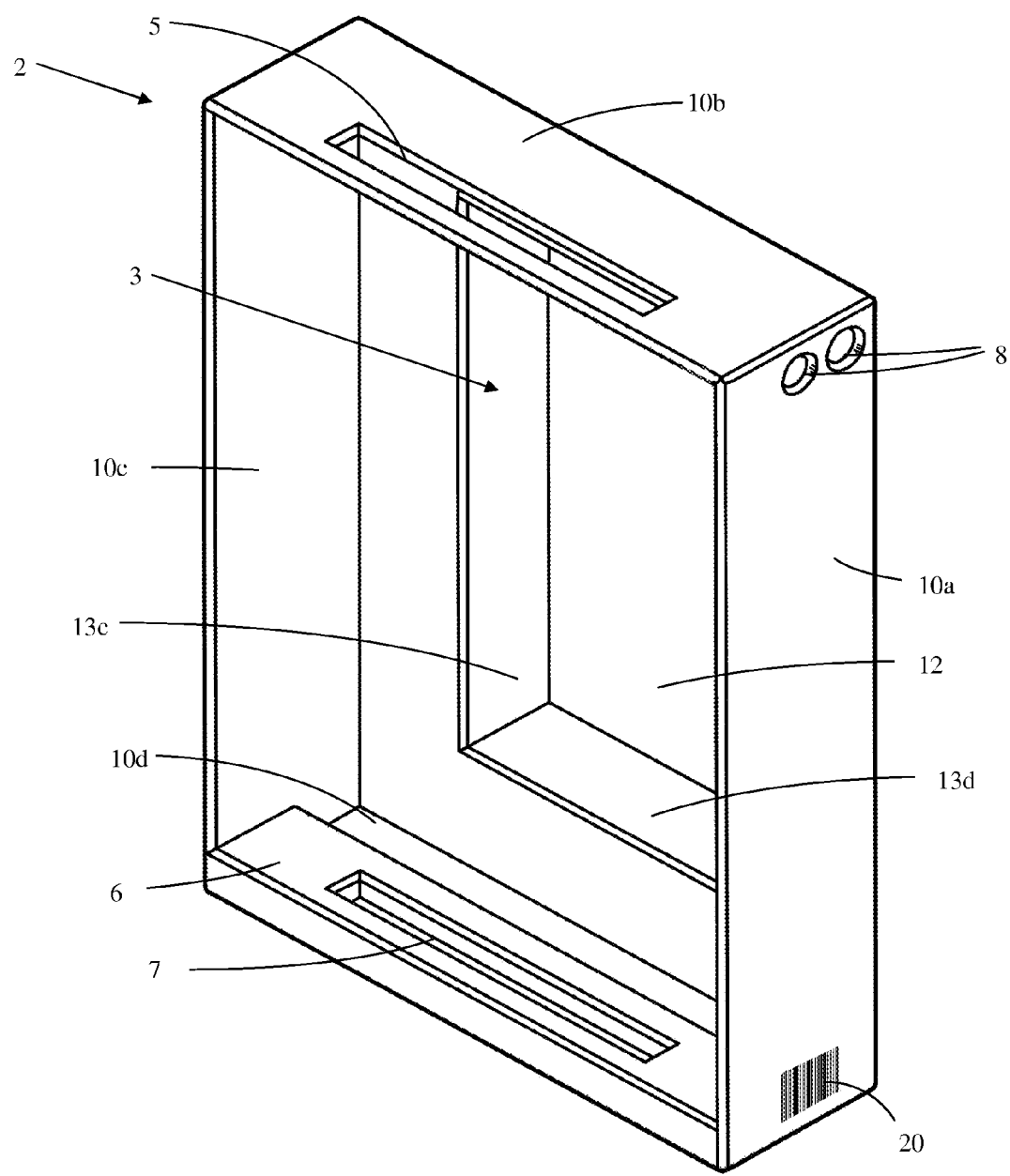
FIG. 2 shows an isometric view of the protective sheath looking at the sheath from a slightly elevated, side angle. The upper slot to accept pathology slide is shown readily visible on the top of the sheath, with the bottom slot shown depicted on the lower wall of the sheath. The paraffin sleeve is seen as an indent in the sheath.
Figure 3:
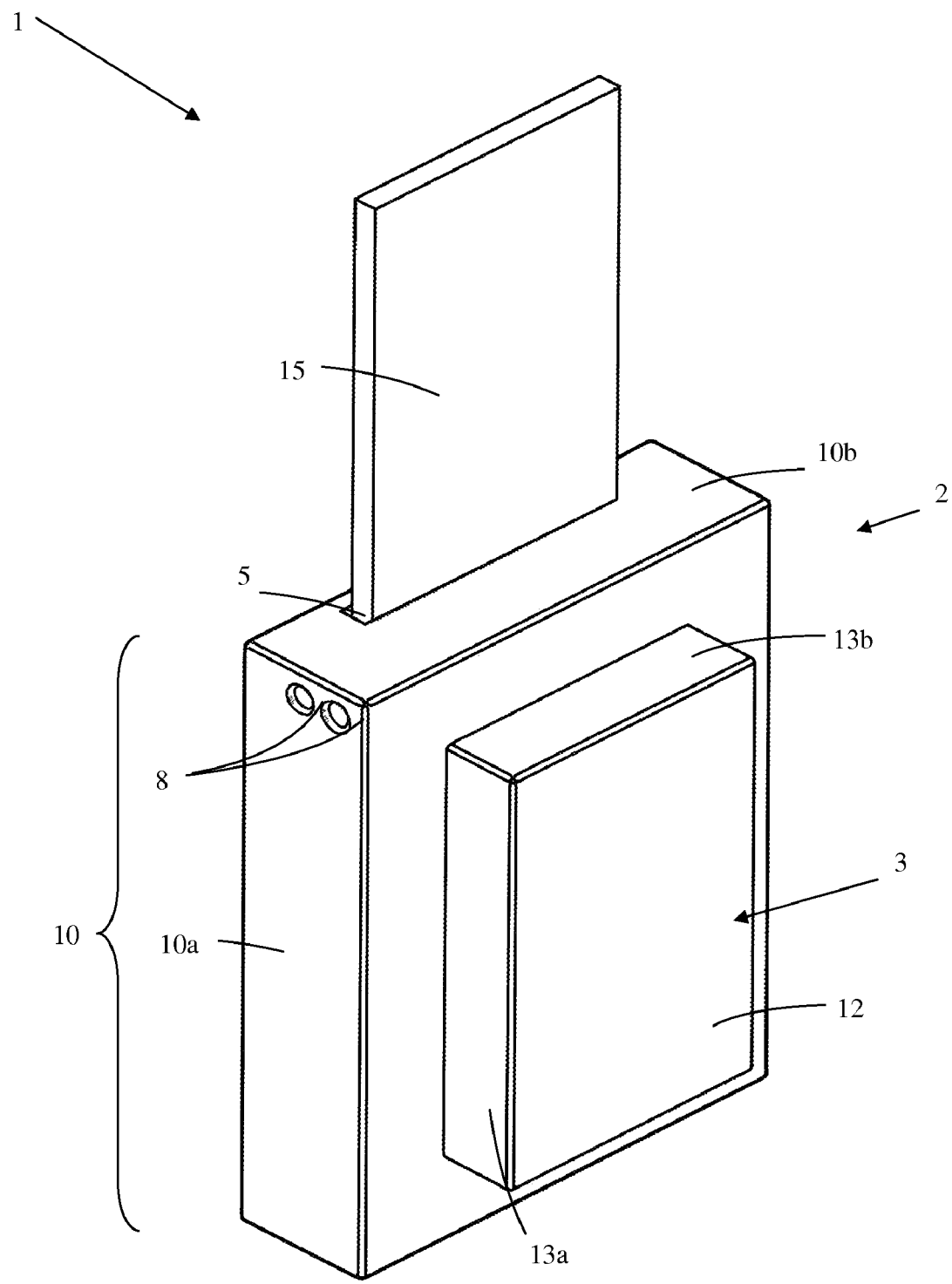
FIG. 3 shows an isometric view of the protective sheath looking at the sheath from above. The upper slot to accept pathology slide is shown readily visible on the top of the sheath. Also shown are the dual holes to permit a robotic arm to position the sheath.

Transverse wall 9 has a cut-out about in the center of the wall. Paraffin block sleeve 3 is disposed on transverse wall 9 adjacent to the cut-out in transverse wall 9 such that paraffin block sleeve 3 and transverse wall 9 forms a continuous element, i.e. there being no openings from the inner space to the outside space between that paraffin block sleeve 3 and transverse wall 9, as seen in FIG. 2. Paraffin block sleeve 3 has a paraffin support transverse wall 12 and first paraffin support horizontal wall 13*a*, upper paraffin support wall 13*b*, second paraffin support horizontal wall 13*c*, and a lower paraffin support wall 13*d*. As seen in FIGS. 1-3, the first paraffin support horizontal wall 13*a*, upper paraffin support wall 13*b*, second paraffin support horizontal wall 13*c*, and lower paraffin support wall are integrated with transverse wall 9. In some embodiments, a tube for air equilibration is disposed on one of the support walls, allowing air to equilibrate while placing and removing the paraffin block and preventing a vacuum build up in the paraffin block support.

To initially store a sample, a paraffin tissue section is placed into paraffin block sleeve 3. Pathology slide 15 is then slid into sheath 1 using upper slot 5, as seen in FIG. 3. The pathology slide is then advanced until the bottom of the slide is received in lower slide opening 7 of lower slide receiving face 6. Once pathology slide 15 is mounted in both upper slide opening 5 and lower slide opening 7, the slide is fixed into position in protective sheath 1. Pathology slide 15 further fixes the position of the paraffin tissue section in the paraffin block sleeve 3.

Figure 4:
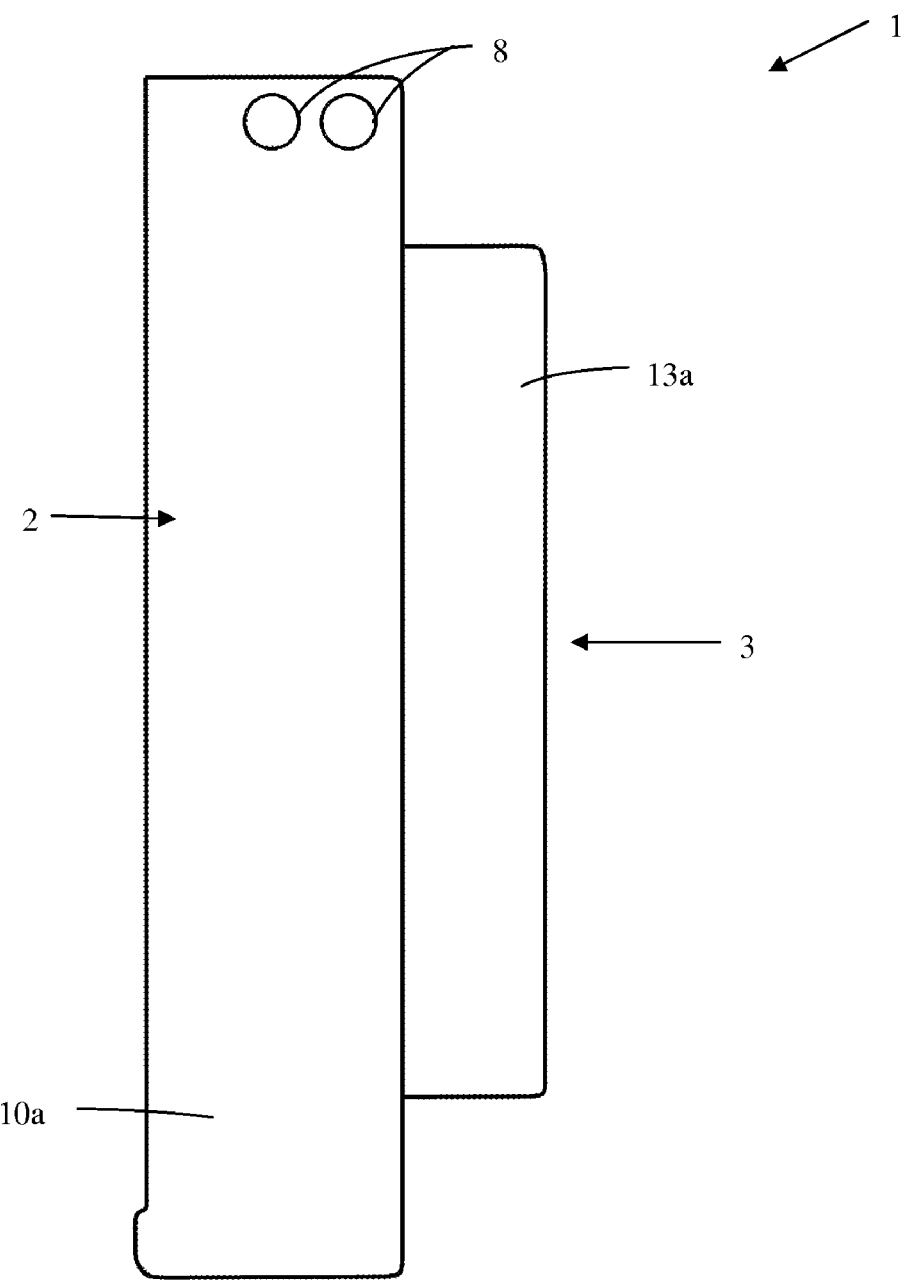
FIG. 4 shows a perspective view of the sheath looking from the side of the invention. The paraffin block sleeve is shown butting from one side of the sheath.

In some embodiments of the invention, handling points 8 are provided to allow a user or automated system to place and retrieve sheath 1, as seen in FIG. 4. Exemplary handling points include dual holes for a robotic arm, hooks, tubes extending from first horizontal wall 10*a* to second horizontal wall 10*c*, and brackets. However, any system known in the art that allows the block to be positioned without concern for the center of gravity is envisioned.

Figure 5:
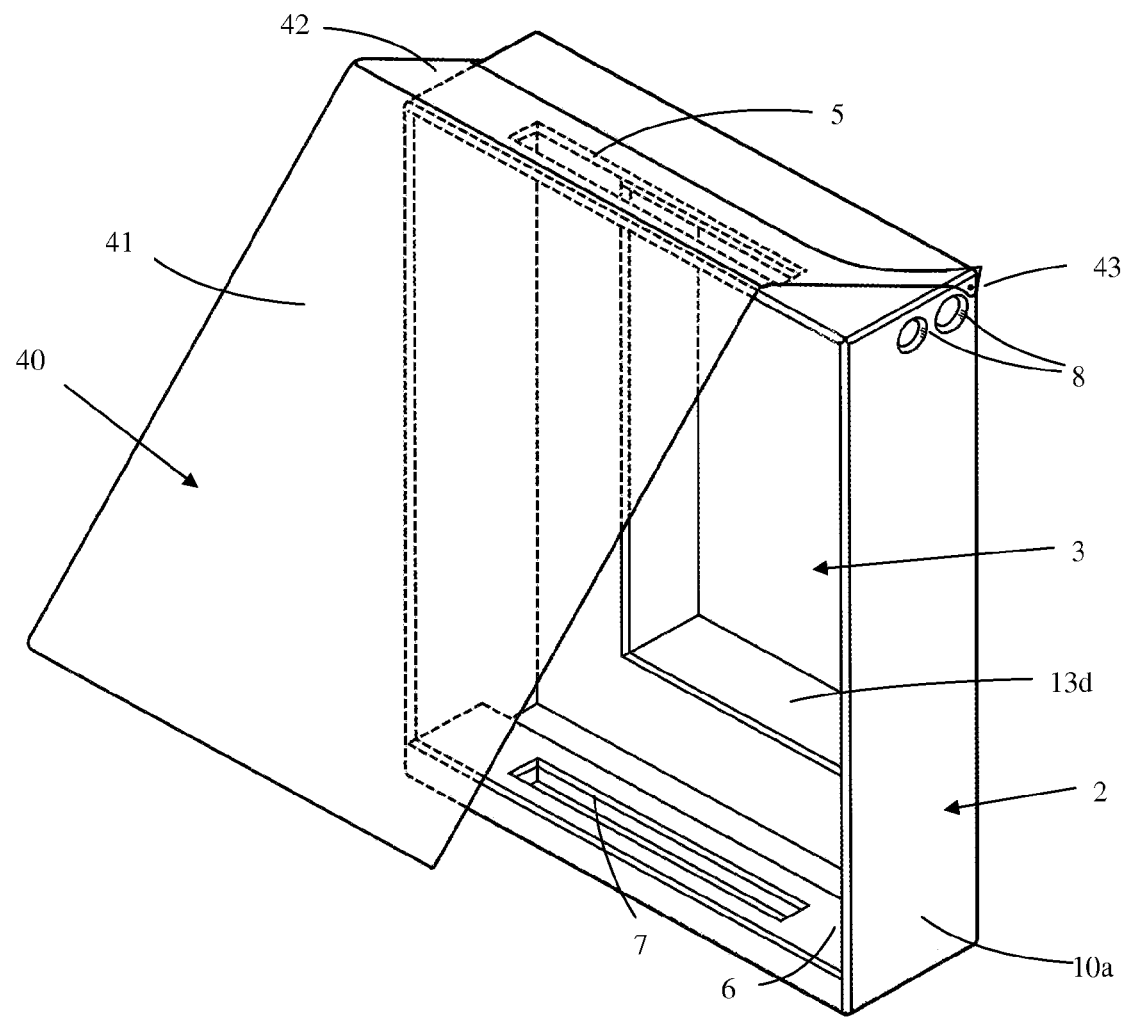
FIG. 5 shows a perspective looking down on the top of the protective sheath.

Advantageously, the sheath may also include a protective face, as seen in FIG. 5. Protective face 40 comprises front protective face 41 and upper protective face 42, which advantageously cover histology slides to prevent damage to the slides, and also prevents the slides from accidental loss by covering upper slide opening 5. When a user needs to recover a histology slide and/or the paraffin block, the user swings protective face 40 toward the back of the sheath, exposing the histology slides and allowing the slides to slide out of upper slide opening 5. Once the histology slides are removed, the user may then access the paraffin block. As seen in FIG. 5, upper protective face 42 covers only a portion of the upper surface of sheath 1 to allow the face to pivot. A section of upper protective face 42 extends to the sides of sheath 1 and hingedly fixes to the sheath, such as through pins, screws, or other means known in the art. Further, where protective face 40 is made of a transparent material, the contents of the sheath may easily be visually inspected. Further, when slides are removed from the sheath, a placeholder, such as a plastic tag, containing information regarding the whereabouts of a slide may be inserted into the slide storage system. The placeholder may have the same dimensions as the slide, such as a plastic rectangle shapes as a slide. The placeholder may either be written on, as with a marker, or contain a space for a paper tag to be slipped into the interior of the placeholder. A transparent protective face allows easy visualization of the information on the placeholder without the need to open the protective face.

The protective sheath is 1.3 inches by 1.8-2.0 inches by 0.7 inches. It is noted that the protective sheath's height may range from 1.7 inches to 2.0 inches.

Example 2

In this embodiment, sheath 1 comprises body 2, histology slide storage sleeve 4, and paraffin block sleeve 3, as seen in FIG. 5. Body 2 includes a transverse wall 9, first horizontal wall 10a, an upper wall 10b, a second horizontal wall 10c, and a lower wall 10d, forming an "open box" and defining an inner space in body 2. Optional identifier 20 is disposed one of the horizontal walls. Handling points 8 are disposed on first horizontal wall 10a and second horizontal wall 10c to allow a user or automated system to retrieve sheath 1. Exemplary handling points include those described in Example 1.

Figure 6:
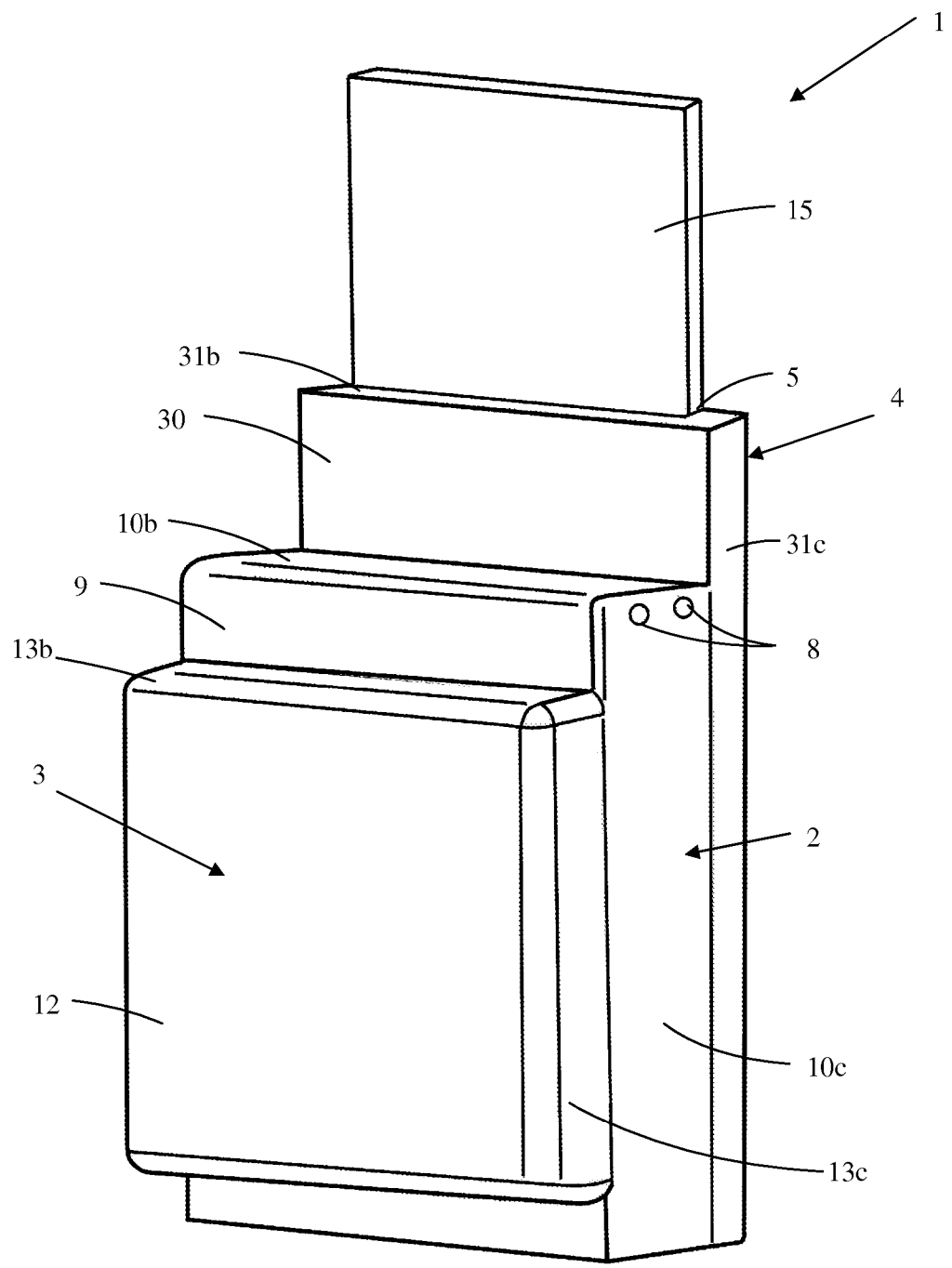
FIG. 6 an isometric view of the protective sheath looking at the sheath from a slightly elevated, side angle. The upper and bottom slot are shown. Also seen is the paraffin sleeve, shown as an indent in the sheath.

Slide storage system 4 comprises slide transverse wall 30, slide horizontal first wall 31a, slide upper wall 31b, slide horizontal second wall 31c, and slide lower wall 31d. Slide transverse wall 30 is disposed on the open face of body 2, and may be the same size as body 2, seen in FIG. 5, or wider than body 2, as indicated in FIG. 6. At least one upper slide opening 5 is disposed on upper wall 10b and dimensioned to accept a pathology slide. Lower slide receiving face 6 is disposed on the inner face of lower wall 10d, providing a surface elevated from lower wall 10d. Lower slide opening 7 is provided in lower slide receiving face 6 and consists of a detent dimensioned to accept a pathology slide.

Paraffin block sleeve 3 has paraffin support transverse wall 12 and first paraffin support horizontal wall 13a, upper paraffin support wall 13b, second paraffin support horizontal wall 13c, and a lower paraffin support wall 13d. Transverse wall 9 has an opening in about in the center of the wall, where paraffin block sleeve 3 is integrated into the transverse wall 9. In some embodiments, a tube for air equilibration is disposed on one of the support walls, allowing air to equilibrate while placing and removing the paraffin block and preventing a vacuum build up in the paraffin block support. As seen in FIGS. 5 and 6, paraffin block sleeve 3 may be the same width as body 2, or narrower than body 2.

Example 3

Figure 7:
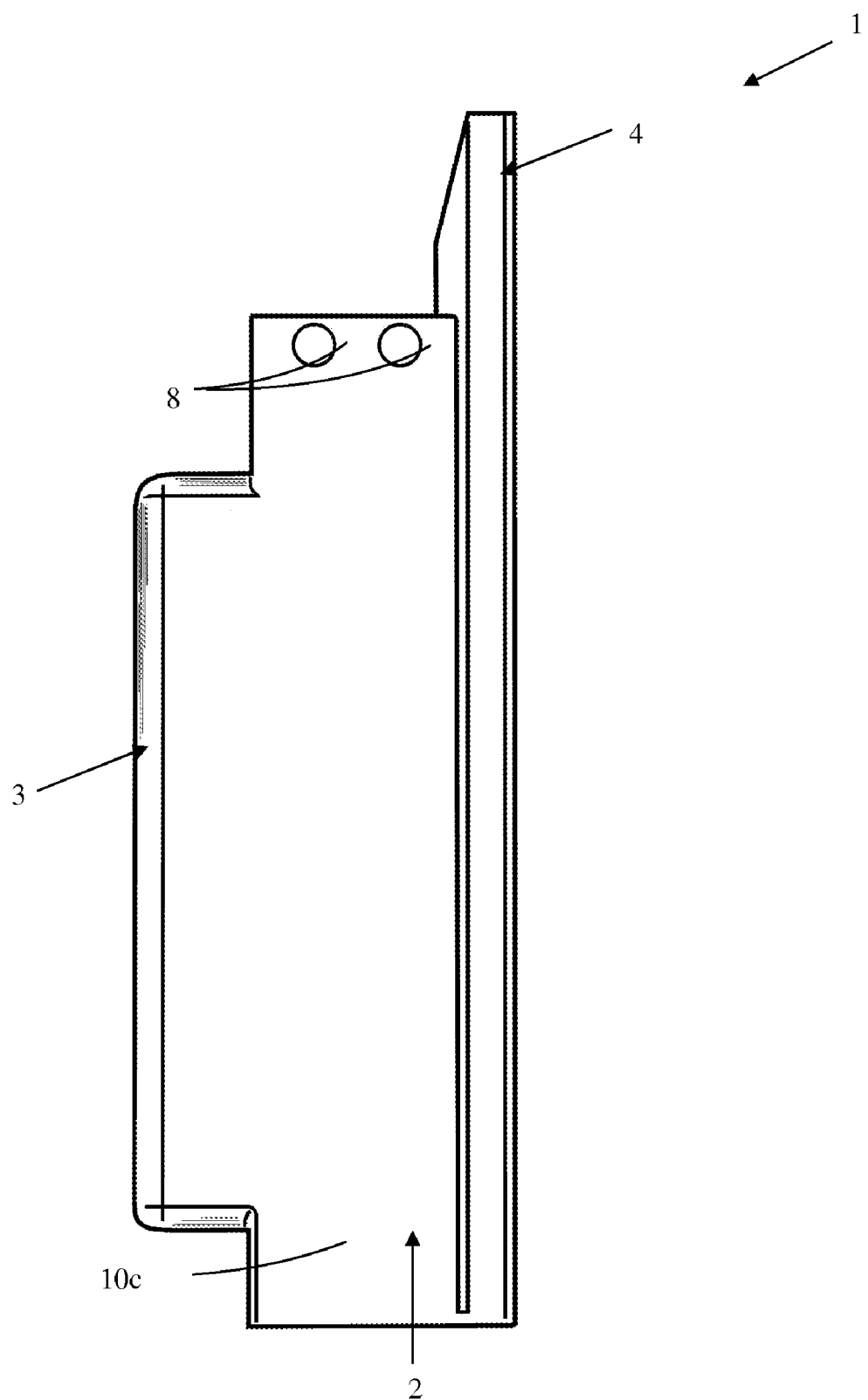
FIG. 7 an isometric view of the protective sheath looking at the back of the sheath from a slightly elevated angle. The external view of the paraffin sleeve is shown, and the pathology slide is shown partially inserted into the upper slot.
Figure 8:
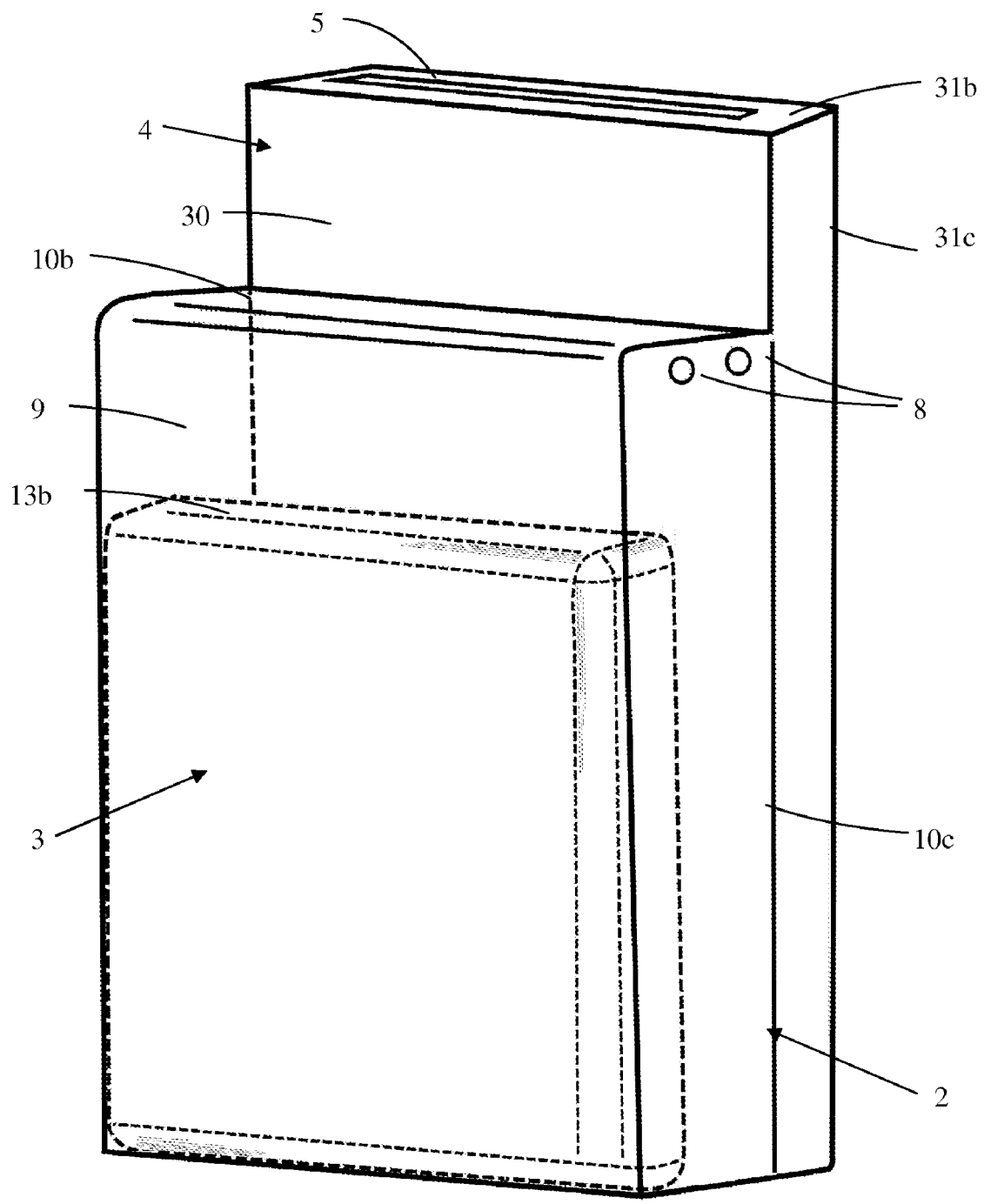
FIG. 8 an isometric wireframe view of the protective sheath looking across the back side of the present invention from a slightly elevated angle. The dual holes are shown extending through the entire width of the sheath to permit a robotic arm to position the sheath, while a simulated pathology slide is depicted in situ.
Figure 9:
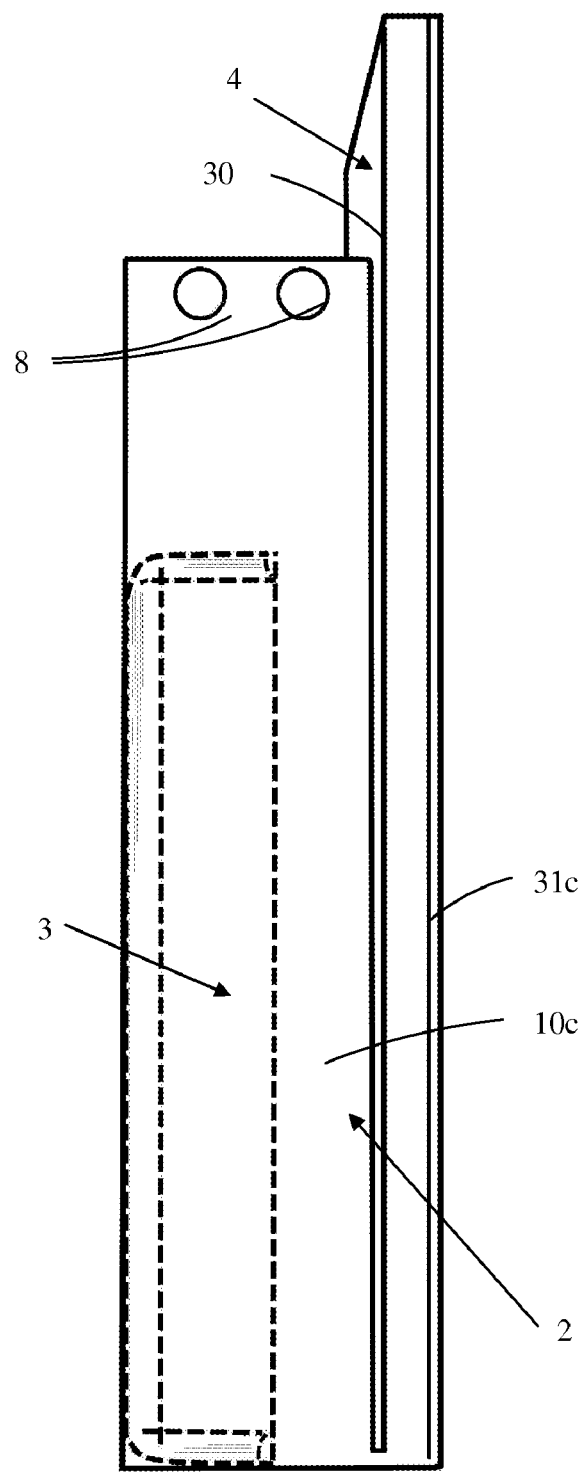
FIG. 9 shows a perspective view of the sheath looking from the side of the invention.

It is noted that this embodiment is similar to Example 2, with the exception that paraffin block sleeve 3 is integrated into the interior space of body 2. The sheath is comprised of body 2 and histology slide storage sleeve 4, as seen in FIG. 7. As in example 2, histology slide storage sleeve 4 may be the same width as body 2, or may be wider than body 2. Paraffin block sleeve 3 is integrated into body 2, seen in FIG. 7. The paraffin block sleeve may use the walls of body 2, i.e. a portion of transverse wall 9, first horizontal wall 10a, second horizontal wall 10c, and lower wall 10d, or may have independent walls to form the paraffin support. Upper paraffin support wall 13b defines the upper-most point of the paraffin block sleeve, and prevents the paraffin block from moving into the upper section of the body, where the handling ports are located, as seen in FIGS. 8 and 9.

Example 4

Figure 10:
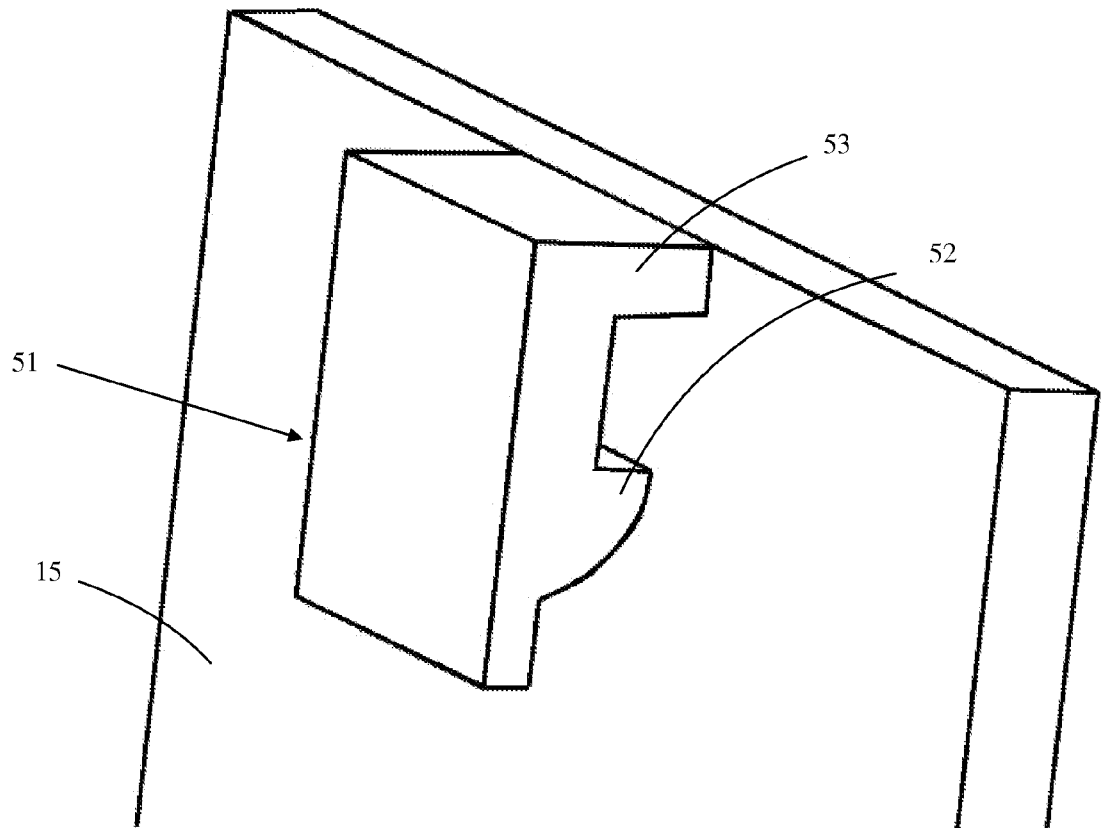
FIG. 10 is an isometric view of the sheath looking from the side of the invention from a slightly elevated, side angle.
Figure 11:
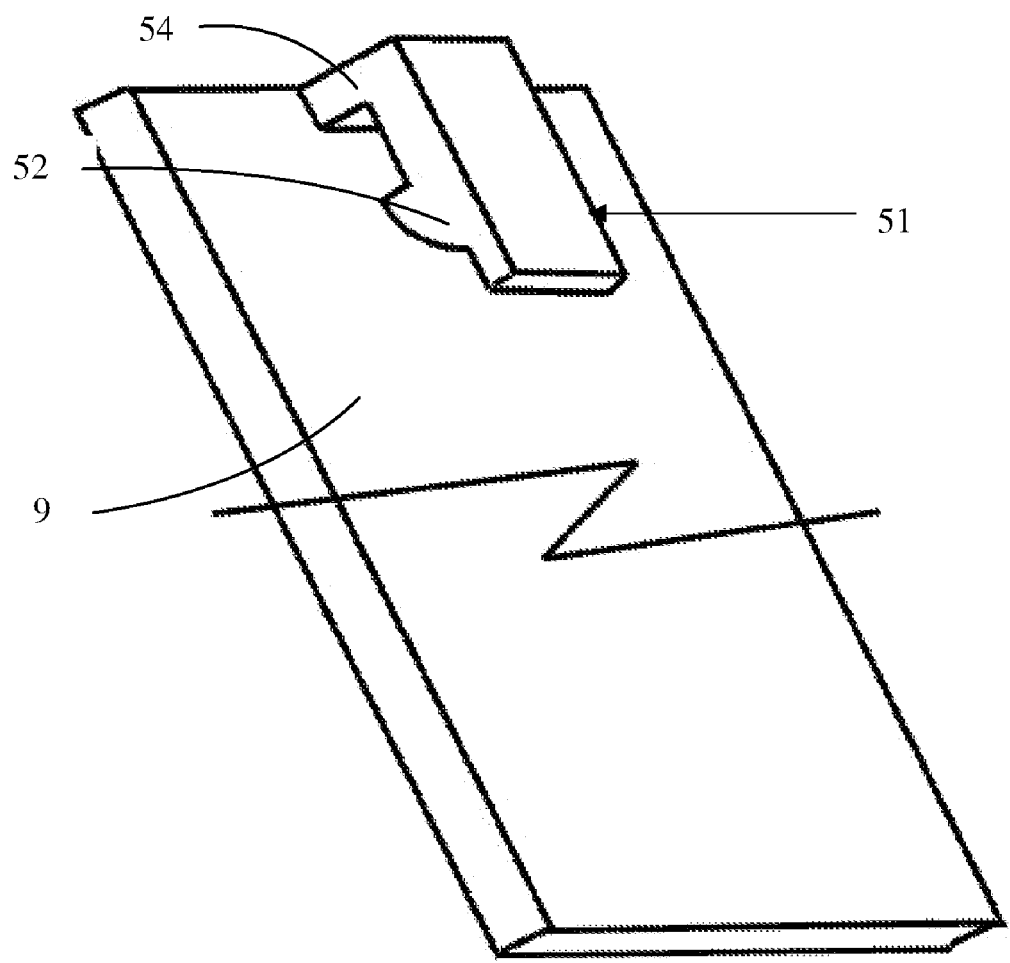
FIG. 11 is an isometric view of a clip embodiment of the retention system with a rounded slide-interacting edge, interacting with a histology slide.
Figure 12:
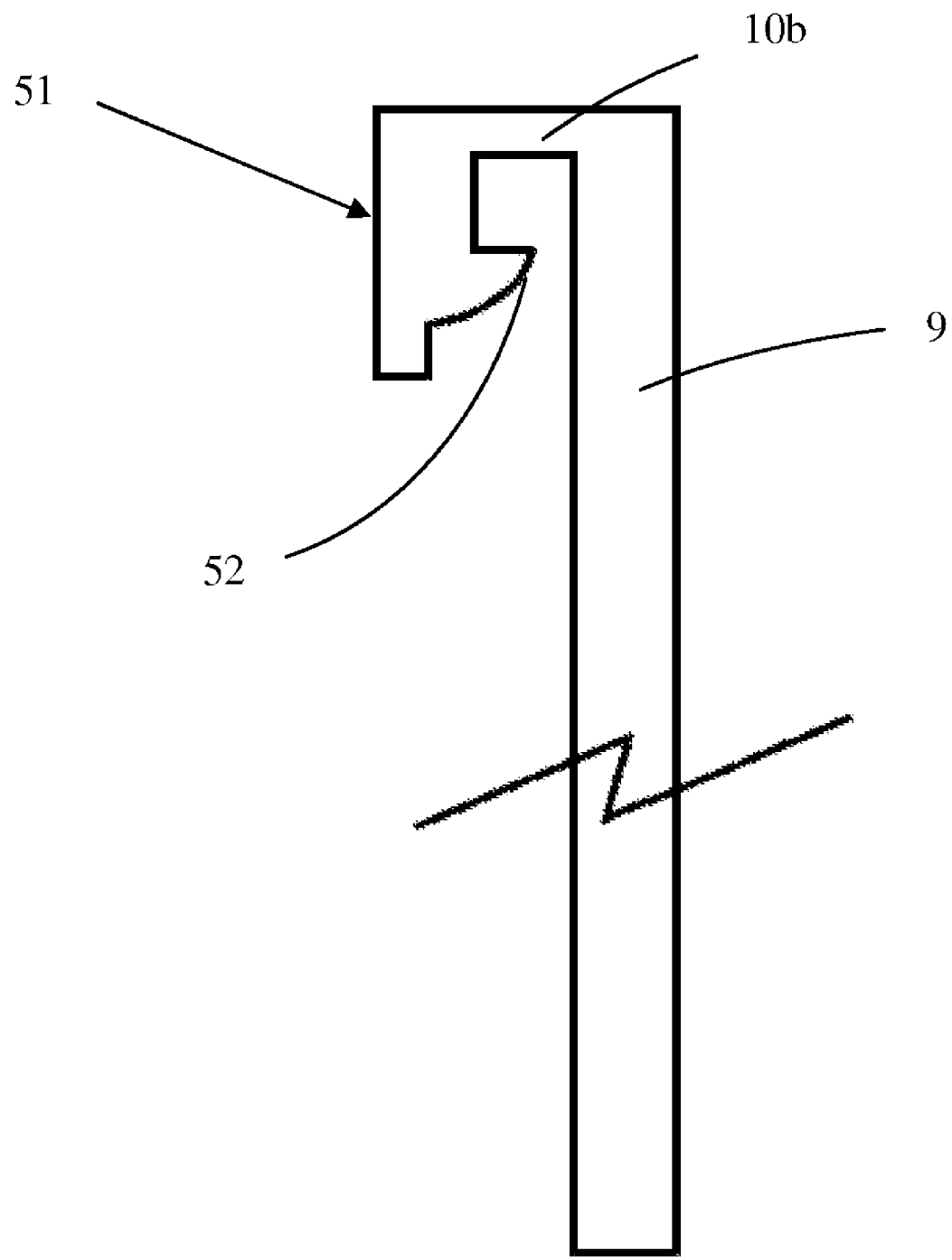
FIG. 12 is a side view of a clip embodiment of the retention system attached to a transverse wall of the sheath.
Figure 13:
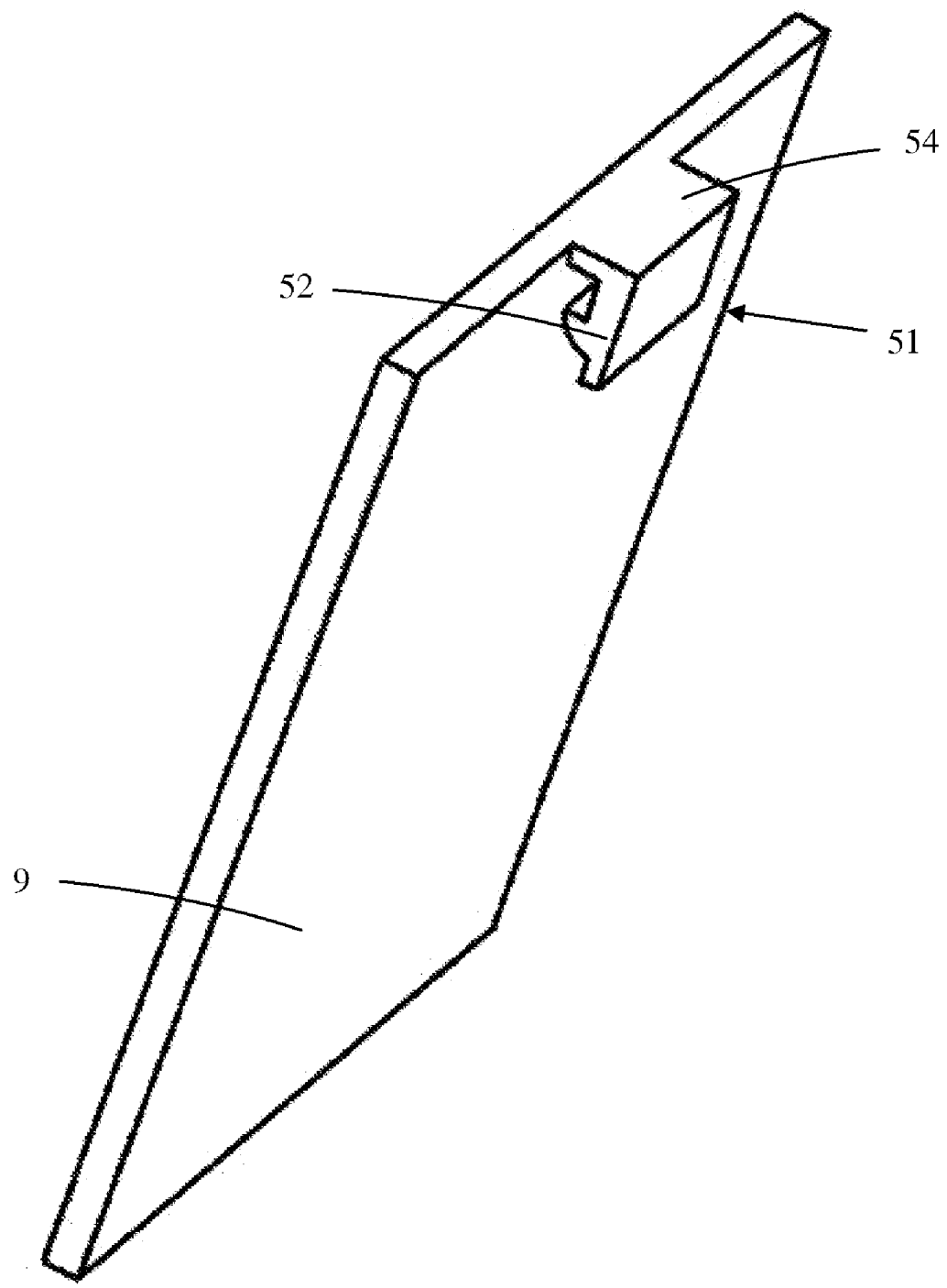
FIG. 13 is an isometric view of a clip embodiment of the retention system attached to a transverse wall of the sheath.
Figure 14:
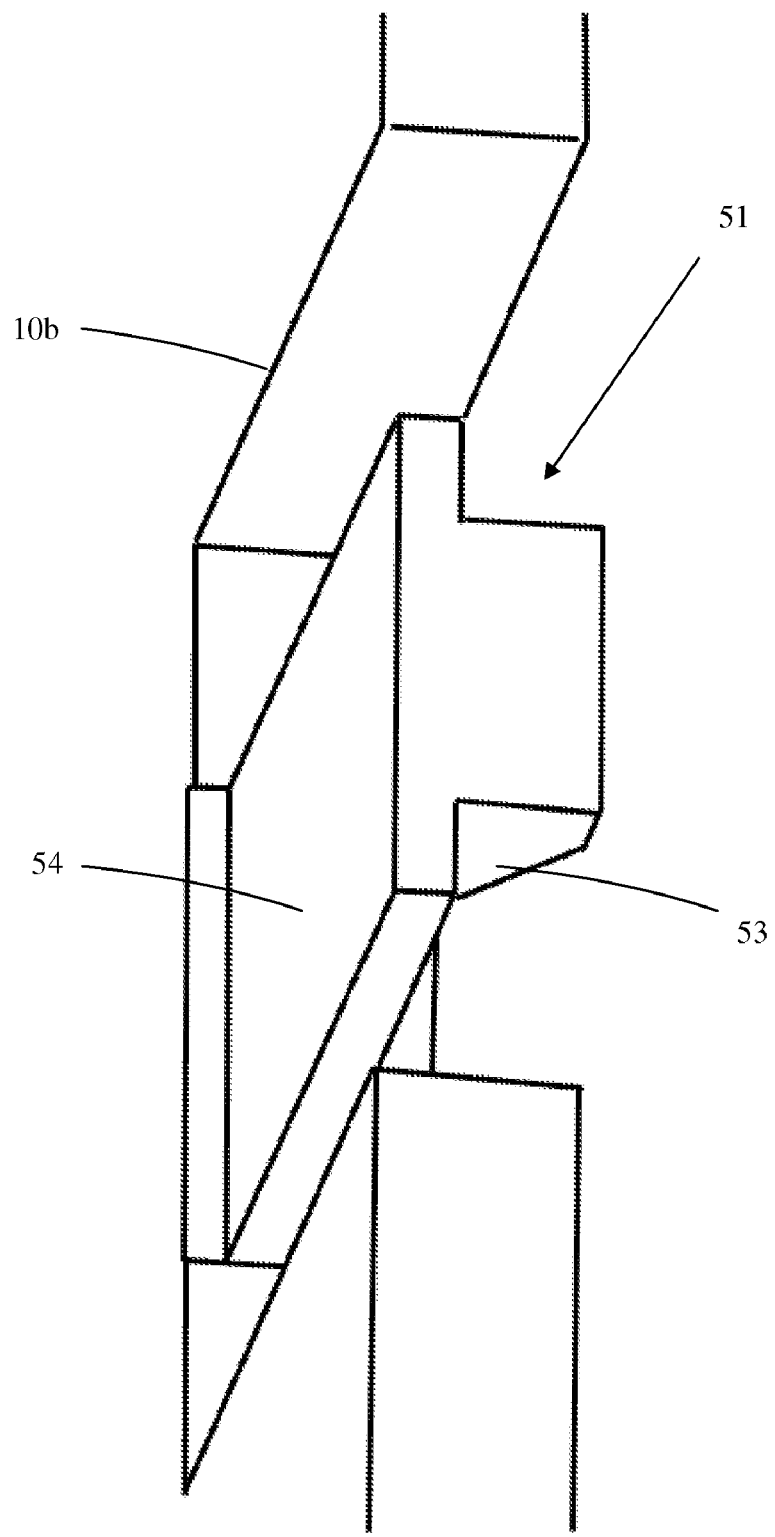
FIG. 14 is an isometric view of a clip embodiment of the retention system with a flat slide-interacting edge, attached to the upper wall of the sheath.
Figure 15:
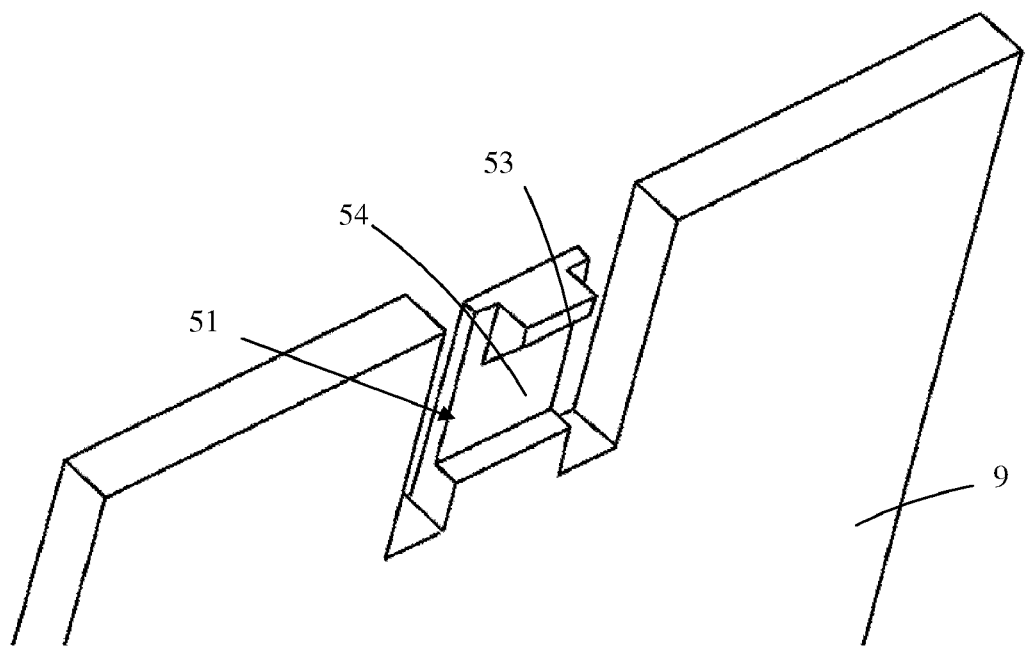
FIG. 15 is an isometric view of a clip embodiment of the retention system with a flat slide-interacting edge, attached to a transverse wall of the sheath.
Figure 16:
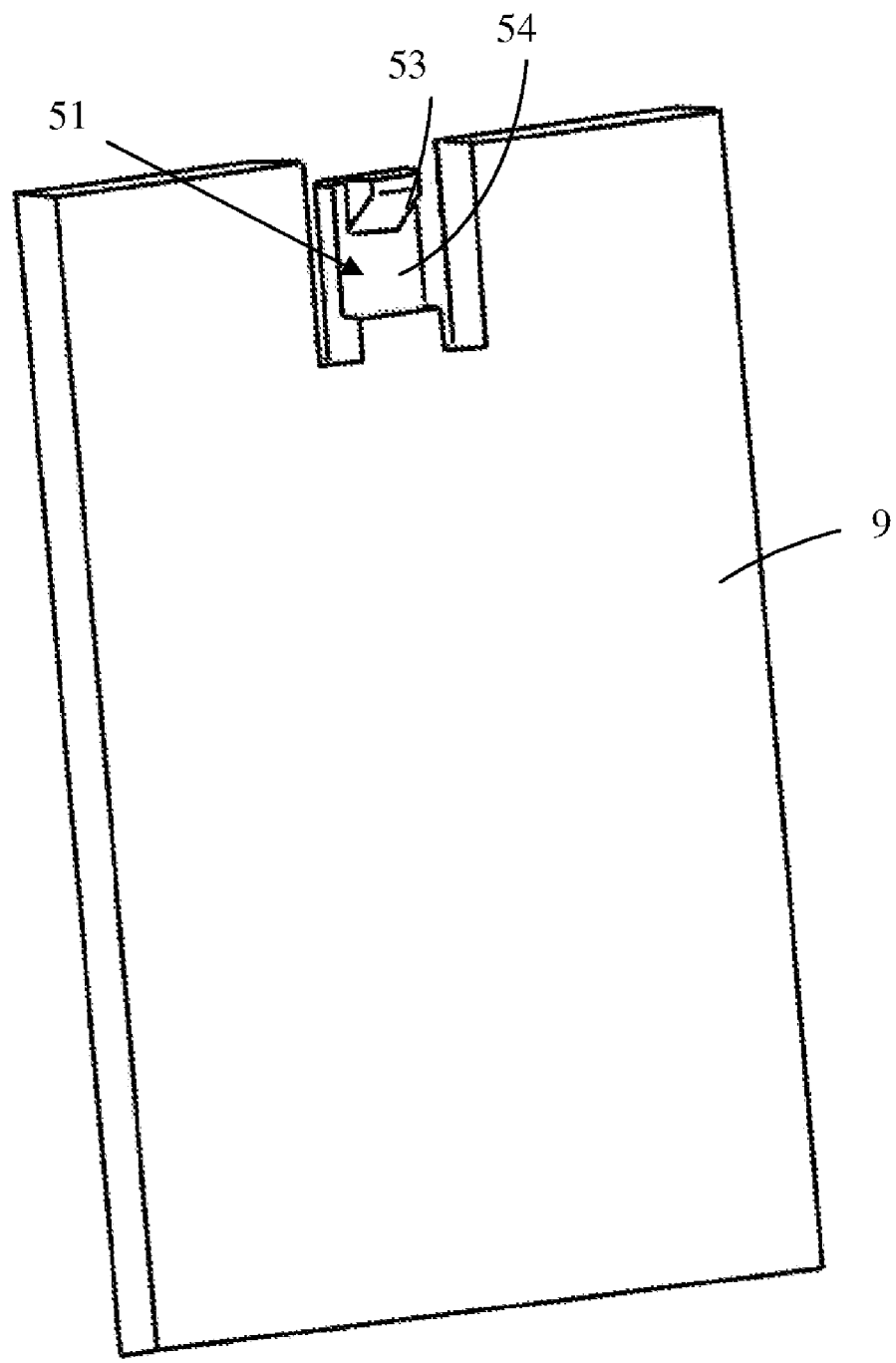
FIG. 16 is an isometric view of a clip embodiment of the retention system with a flat slide-interacting edge, attached to a transverse wall of the sheath.
Figure 17:
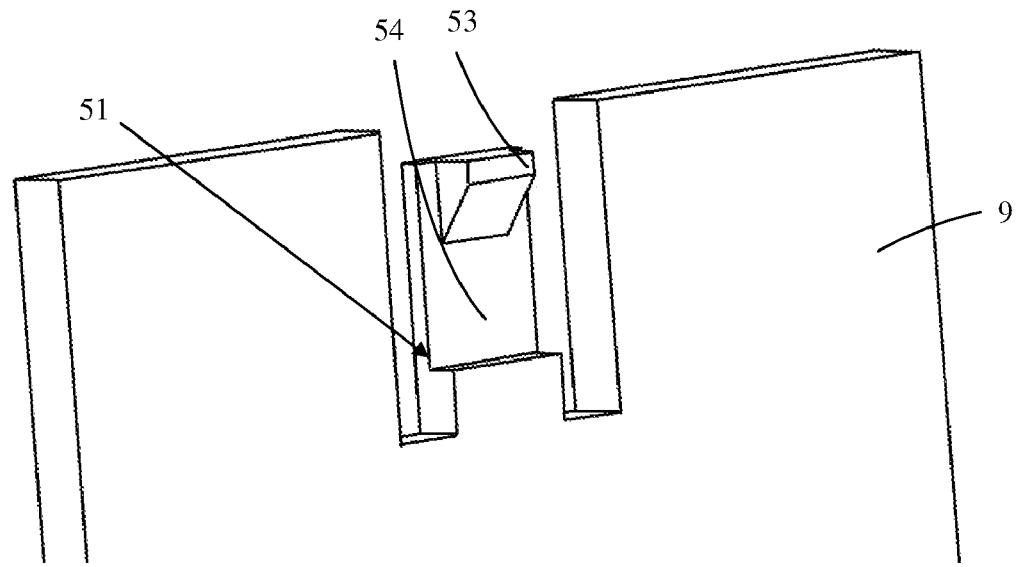
FIG. 17 is an isometric view of a clip embodiment of the retention system with a flat slide-interacting edge, attached to a transverse wall of the sheath.
Figure 18:
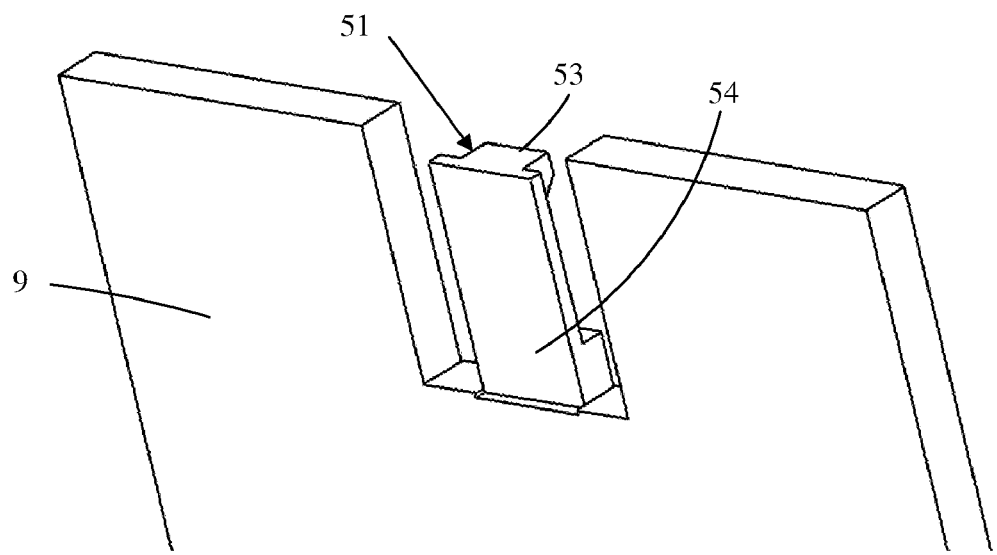
FIG. 18 is an isometric view of a clip embodiment of the retention system with a flat slide-interacting edge, attached to a transverse wall of the sheath.

The sheath, including any of the embodiments above, may include retention system 51. Retention system 51 may be mounted horizontally or vertically and may include systems known in the art. Further, the retention system may be integral to the sheath, using the modulus of elasticity for the material the retention system and sheath are composed from, or may use a spring or other similar device known in the art. Angled face 52, seen in FIG. 10, is rounded to interact with the face of the slide and allow the top of slide 15 to be easily separated from slide retainer 53 by a user. The user moves retention system 51 from a locking position to an access position by pushing the top of the clip. This exposes the upper slide opening and allows a slide to be added or removed from the sheath. The user then releases the retention system, causing the retention system to return to the locking position, and allowing slide retainer 53 to engage the top of slide 15. In some embodiments, the retention system is attached to a vertical surface, such as transverse wall 9 (Examples 1 and 3), or transverse wall 30 (Example 2), as seen in FIG. 11. Angled face 52 in these embodiments may function as slide retainer 53, holding the slide into position. Where retention system 51 is integrated into sheath 1, the interconnection acts as retention spring 54. Alternatively, retention system 51 may be connected to upper wall 10b, or horizontal surface, as seen in FIGS. 12 and 13. Where retention system 51 is connected to upper wall 10b, the retention system may be integrated into the upper wall, with the interconnection acting as retention spring 54 as seen in FIG. 14.

The clip or other retention system may have a flat, angled face, allowing the slide to push the retention system away from the upper slide opening when being inserted, as seen in FIGS. 15-18. This embodiment of the retention system, with a flat angled face, allows the slide to push the retention system away from the upper slide opening when being inserted. The adjacent face is flat, to interact with the top of the slide.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a histology slide and paraffin block sleeve, it will be apparent to those skilled in the art that variations and modifications are possible without deviating from the broad spirit and principle of the present invention. It is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. A protective sheath, comprising
a first protective member, wherein the first protective member further comprises
   a first and second vertical walls, having an upper edge, a lower edge, a transverse edge and an opening edge;
   a first upper horizontal wall disposed on the upper edge of the first and the second vertical walls;
   a first lower horizontal wall disposed on the lower edge of the first and the second vertical walls;
   a first transverse wall disposed on the transverse edge of the first and the second vertical walls, wherein the walls define a box and wherein the first and second vertical walls are substantially the same size;
   at least one opening disposed in the upper horizontal wall and adapted to accept a tissue slide; and
a second protective member disposed on the transverse wall of the first protective member, further comprising
   a third vertical wall and fourth vertical wall having an upper edge, a lower edge, and a transverse edge;
   a second upper horizontal wall disposed on the upper edge of the third vertical wall and fourth vertical wall;
   a second lower horizontal wall disposed on the lower edge of the third vertical wall and fourth vertical wall;
   a second transverse wall disposed on the transverse edge of the third and the fourth vertical walls, wherein the walls define a box and wherein the third and fourth vertical walls are substantially the same size;
   where the second protective member is adapted to accept a paraffin block.

2. The protective sheath of claim 1, further comprising at least one slot disposed on the lower horizontal wall and adapted to accept a tissue slide.

3. The protective sheath of claim 1, further comprising a coating on the edges of the at least one opening adapted to accept a tissue slide, wherein the coating is Teflon, polyester, para-phenylenediamine, terephthaloyl chloride polymer, carbon fiber, expanded PTFE, meta-phenylenediamine, nylon, polypropylene, latex, silicone, polyurethane, polyisoproprene polyvinylchloride, ethylene propylene diene monomer, styrene, cornstarch powder, graphite, meta-aramid compounds, or para-aramid compounds.

4. The protective sheath of claim 1, further comprising at least one handling point disposed on the first and the second vertical walls, or disposed on the third and the fourth vertical walls.

5. The protective sheath of claim 4, wherein the at least one handling point is a plurality of holes, at least one handle, at least one hook, at least one bracket, or a plurality of tubes extending from the first vertical wall to the second vertical wall.

6. The protective sheath of claim 1, wherein the second protective member is dimensioned to accept a paraffin block.

7. The protective sheath of claim 1, further comprising a retention system, wherein the retention system comprises
   a connecting member having a first end and a second end, wherein the first end is disposed on the first upper horizontal wall or first transverse wall;
   an angled face disposed on the second end of the connecting member;
   and wherein the retention system is integrated into the first upper horizontal wall or first transverse wall, or mounted to the first upper horizontal wall or first transverse wall.

8. The protective sheath of claim 7, further comprising a spring in mechanical communication with the connecting member, such that the spring orients the connecting member in a first position.

9. The protective sheath of claim 7, wherein the angled face is rounded to interact with a histology slide.

10. The protective sheath of claim 7, wherein the angled face is flat to interact with a histology slide.

11. The protective sheath of claim 1, further comprising at a paraffin support structure disposed in the interior of the second protective member, wherein the paraffin support structure comprises
   an integrated support, further comprising
      a support wall disposed on the interior face of the third and fourth vertical walls, such that the space defined between the third and fourth vertical walls and the second lower horizontal wall and the support wall are dimensioned to accept a paraffin block;
   a partially integrated support further comprising
      a fifth and sixth vertical walls disposed in the interior space of the second protective member, having an upper edge and a lower edge;
      a first support wall disposed on the upper edge of the fifth vertical wall and sixth vertical wall;
      a second support wall disposed on the lower edge of the fifth vertical wall and sixth vertical wall;
      where the support walls and fifth and sixth vertical walls are disposed on the second transverse wall, and wherein the partially integrated support is dimensioned to accept a paraffin block; or
   a distinct support attached to the second support, further comprising
      a fifth and sixth vertical walls disposed in the interior space of the second protective member, having an upper edge, a lower edge, and a transverse edge;
      a first support wall disposed on the upper edge of the fifth vertical wall and sixth vertical wall;
      a second support wall disposed on the lower edge of the fifth vertical wall and sixth vertical wall;
      a third transverse wall disposed on the transverse edge of the fifth and sixth vertical walls;
      where the third transverse wall is disposed on the second transverse wall, and wherein the fifth and sixth vertical walls, first and second support walls, and third transverse wall are dimensioned to accept a paraffin block.

12. The protective sheath of claim 1, wherein the sheath is constructed of plastic, polyethylene, polypropylene, polyethylene terephthalate, polyvinylchloride, polyvinylidenechloride, polycarbonate, polyurethane, polyamide, polytetrafluoroethylene, polyvinylacetate, wood, ceramic, cardboard, fiberboard, metal, titanium, stainless steel, or surgical steel.

13. The protective sheath of claim 1, further comprising a protective shield, wherein the protective shield is
   a hingedly connected protective shield further comprising
      a first face adapted to hingedly engage the first upper horizontal wall;
      a second face disposed perpendicular to the first face and adapted to cover the open face of the first protective member; or
   a slidingly connected protective shield, further comprising
      a pair of rails disposed on the first and second vertical walls along the open face of the first and second vertical walls; and a protective face adapted to engage the pair of rails.

14. The protective sheath of claim 13, wherein the protective shield hingedly engages using pins, screws, or hinges.

15. The protective sheath of claim 13, wherein the protective face is constructed of polyethylene, polypropylene, polyethylene terephthalate, polyvinylchloride, polyvinylidenechloride, polycarbonate, polyurethane, polyamide, polytetrafluoroethylene, polyvinylacetate, wood, ceramic, cardboard, fiberboard, metal, titanium, stainless steel, or surgical steel.

16. A protective sheath, comprising
a first protective member, wherein the first protective member further comprises
a first and second vertical walls, having an upper edge, a lower edge, a transverse edge and an opening edge;
a first upper horizontal wall disposed on the upper edge of the first and the second vertical walls;
a first lower horizontal wall disposed on the lower edge of the first and the second vertical walls;
a first transverse wall disposed on the transverse edge of the first and the second vertical walls, wherein the walls define a box and wherein the first and second vertical walls are substantially the same size;
at least one opening disposed in the upper horizontal wall and adapted to accept a tissue slide;
a sheath body further comprising
a third vertical wall and fourth vertical wall, having an upper edge, a lower edge, a transverse edge and an opening edge, where the opening edge is disposed on the first transverse wall;
a second upper horizontal wall disposed on the upper edge of the third and the fourth vertical walls;
a second lower horizontal wall disposed on the lower edge of the third and the fourth vertical walls;
a second transverse wall disposed on the transverse edge of the third and the fourth vertical walls, wherein the walls define a box and wherein the third and the fourth vertical walls are substantially the same size;
at least one handling point disposed on the third and the fourth vertical walls; and
a second protective member disposed on the second transverse wall of the sheath body, further comprising
a fifth vertical wall and sixth vertical wall having an upper edge, a lower edge, a transverse edge and an opening edge, where the opening edge is disposed on the second transverse wall
a third upper horizontal wall disposed on the upper edge of the fifth vertical wall and sixth vertical wall;
a third horizontal wall disposed on the lower edge of the fifth vertical wall and sixth vertical wall;
a third transverse wall disposed on the transverse edge of the fifth vertical wall and sixth vertical walls, wherein the walls define a box and wherein the fifth vertical wall and sixth vertical walls are substantially the same size;
where the second protective member is dimensioned and adapted to accept a paraffin block.

17. The protective sheath of claim 16, further comprising at least one slot disposed on the lower horizontal wall and adapted to accept a tissue slide.

18. The protective sheath of claim 17, further comprising a coating on the edges of the at least one slot disposed on the lower horizontal wall, wherein the coating is Teflon, polyester, para-phenylenediamine, terephthaloyl chloride polymer, carbon fiber, expanded PTFE, meta-phenylenediamine, nylon, polypropylene, latex, silicone, polyurethane, polyisoproprene polyvinylchloride, ethylene propylene diene monomer, styrene, cornstarch powder, graphite, meta-aramid compounds, or para-aramid compounds.

19. The protective sheath of claim 16, further comprising a coating on the edges of the at least one opening adapted to accept a tissue slide, wherein the coating is Teflon, polyester, para-phenylenediamine, terephthaloyl chloride polymer, carbon fiber, expanded PTFE, meta-phenylenediamine, nylon, polypropylene, latex, silicone, polyurethane, polyisoproprene polyvinylchloride, ethylene propylene diene monomer, styrene, cornstarch powder, graphite, meta-aramid compounds, or para-aramid compounds.

20. The protective sheath of claim 16, wherein the at least one handling point is a plurality of holes, at least one handle, at least one hook, at least one bracket, or a plurality of tubes extending from the first vertical wall to the second vertical wall.

21. The protective sheath of claim 16, wherein the sheath is constructed of plastic, polyethylene, polypropylene, polyethylene terephthalate, polyvinylchloride, polyvinylidenechloride, polycarbonate, polyurethane, polyamide, polytetrafluoroethylene, polyvinylacetate, wood, ceramic, cardboard, fiberboard, metal, titanium, stainless steel, or surgical steel.

22. The protective sheath of claim 16, further comprising a retention system, wherein the retention system comprises
a connecting member having a first end and a second end, wherein the first end is disposed on the first upper horizontal wall or first transverse wall;
an angled face disposed on the second end of the connecting member;
and wherein the retention system is integrated into the first upper horizontal wall or first transverse wall, or mounted to the first upper horizontal wall or first transverse wall.

23. The protective sheath of claim 22, further comprising a spring in mechanical communication with the connecting member, such that the spring orients the connecting member in a first position.

24. The protective sheath of claim 22, wherein the angled face is rounded to interact with a histology slide.

25. The protective sheath of claim 22, wherein the angled face is flat to interact with a histology slide.

26. The protective sheath of claim 16, further comprising a protective shield, wherein the protective shield is
a hingedly connected protective shield further comprising
a first face adapted to hingedly engage the first upper horizontal wall;
a second face disposed perpendicular to the first face and adapted to cover the open face of the first protective member; or
a slidingly connected protective shield, further comprising
a pair of rails disposed on the first and second vertical walls along the open face of the first and second vertical walls; and
a protective face adapted to engage the pair of rails.

27. The protective sheath of claim 26, wherein the protective shield hingedly engages using pins, screws, or hinges.

28. The protective sheath of claim 26, wherein the protective face is constructed of polyethylene, polypropylene, polyethylene terephthalate, polyvinylchloride, polyvinylidenechloride, polycarbonate, polyurethane, polyamide, polytetrafluoroethylene, polyvinylacetate, wood, ceramic, cardboard, fiberboard, metal, titanium, stainless steel, or surgical steel.

* * * * *